United States Patent [19]

Sawyer et al.

[11] 4,027,392
[45] June 7, 1977

[54] ENDOSTEAL BIONIC TOOTH AND IMPLANTATION METHOD

[75] Inventors: Philip Nicholas Sawyer; Boguslaw Stanczewski, both of Brooklyn, N.Y.

[73] Assignee: Interface Biomedical Laboratories Corporation, Brooklyn, N.Y.

[22] Filed: May 10, 1976

[21] Appl. No.: 684,767

[52] U.S. Cl. ............................................. 32/10 A
[51] Int. Cl.² ...................................... A61C 13/00
[58] Field of Search .................. 32/10 A; 3/1.9; 128/82.1

[56] References Cited

UNITED STATES PATENTS

| | | | |
|---|---|---|---|
| 3,745,995 | 7/1973 | Kraus | 3/1.9 |
| 3,892,648 | 7/1975 | Phillips | 128/82.1 |
| 3,918,440 | 11/1975 | Kraus | 128/82.1 |
| 3,968,790 | 7/1976 | Fukada | 3/1.9 |

*Primary Examiner*—Robert Peshock
*Attorney, Agent, or Firm*—Roberts & Cohen

[57] ABSTRACT

An endosteal tooth in one form is made of an electrically conductive material and is provided with an implant (e.g., lower) socket portion and a removably mounted crown (e.g., upper) portion which houses therein a source of electrical current for the implant socket portion. By supplying electrical current or voltage to the implant socket portion, which is embedded in bone in the region of the implantation, the growth of bone is induced and the prevention of infection provided. The rate of growth of the bone and the type of bone growth can be controlled by the amount of current supplied to the implant socket portion. In one embodiment of the invention, the source of electrical current is housed in the crown portion of the tooth which is replaced with a final crown after the growth of bone has been completed. In another form of the invention, the source of electrical current is supplied externally of the tooth. According to different procedures of the invention, current or voltage can be supplied by battery, thermocouple junction or by immersing contacting metals in body fluids.

18 Claims, 3 Drawing Figures

ENDOSTEAL BIONIC TOOTH AND IMPLANTATION METHOD

FIELD OF THE INVENTION

This invention is directed to novel prosthetic dentures and procedures to improve techniques by which an artificial tooth is implanted by submucosal, subperiosteal, endosseous techniques or the like.

BACKGROUND OF THE INVENTION

The implantation of teeth has been known for many years. One of the first techniques employed involved the replacement of human teeth with heteraltopic teeth of calves or sheep.

In modern times, implantation is carried out with prosthetic teeth made of ceramic materials which are sturdy and resistant to fracture and wear. Modern implantation techniques include simple submucosal attachment to underlying bones, subperiosteal fixation, and endosseous implantation.

Examples of these methods are, for instance, disclosed in the following articles: "The Blade Vent— A New Dimension in Endosseous Implantology" by Leonard I. Linkow, in Volume 11, Spring 1968 issue of *DENTAL CONCEPTS*, pages 3–12; "Historpathologic and Radiologic Studies on Endosseous Implants" by Leonard I. Linkow, in Volume 11, Summer 1968 issue of *DENTAL CONCEPTS*, pages 3–13; "Mouth Reconstruction for the Edentulous Maxilla Using Endosseous Blades" by Leonard I. Linkow, in Volume 12, Winter 1969 issue of *DENTAL CONCEPTS*, pages 3–21; "Various Applications of Endosseous Implants" by Anthony J. Viscido, in Volume 75, October 1969 issue of *DENTAL DIGEST*, pages 398–406; "Implants and Transplants-An aid to Assisting the Dental Cripple" by Morris J. Baskas and Sidney I. Berger, in Volume 39, July 1970 issue of *THE DENTAL ASSISTANT*, pages 12–15: "Endosseous Blade Implants: Technique for Abutments in Fixed Prosthodontics" by Anthony J. Viscido, in Volume 78, February 1972 issue of *DENTAL DIGEST*, pages 64–75; "The Two Stage Palato-Labial Juxta-Endosteal Implant Intervention for Severely Atrophied Edentulous Maxillae", by Leonard I. Linkow, Volume 12, Spring 1972 issue of *DENTAL CONCEPTS*, pages 2–13.

Despite the accumulation of improved techniques and experience, however, known methods of implantation, and the various prosthetic tooth forms that accompany the methods, are characterized by the disadvantages of being highly susceptible to boney elisis accompanied by infection as the complication proceeds.

By way of further background to the invention, the use of electrical energy to induce the growth of callus has been adequately disclosed in the following articles: "Mechanical and Electrical Callus," by Iwao Yasuda, in Volume 238 19anyaa 9238 of the *ANNALS OF THE NEW YORK ACADEMY OF SCIENCES*, pages 457–464; "Electrical Stimulation of Arricular Cartilage Regeneration" by Bruce Baker, pages 491–499 of the above publication; "Effects of Electrode Placement on Stimulation of Adult Frog Limb Regeneration," by Stephen D. Smith, pages 500–507 of the above publication; and "Mechanism of Electrical Stimulation of Bone Formation," by Lewis Klapper and Richard E. Stallard, pages 530–539 of the publication. Further, the article entitled "The Influence of Electrical Current on an Infecting Microorganism in Wounds," by Lester E. Wolcott, published in the above-noted publication on pages 543–551 discloses the beneficial effect of electrical current for preventing infection. The article entitled "The use of Telemetry in Prosthetics," by E. A. Wain, published in Volume 20, Number 4, December 1969 issue of *THE DENTAL PRACTITIONER*, discloses the use of a transmitter device in a prosthetic device which is used to measure oral pressures.

SUMMARY OF THE INVENTION

It is an object of the invention to provide improved techniques for the implantation of teeth.

It is another object of the invention to provide an improved prosthetic tooth for implantation which is long lasting, less prone to infection, and which assists in the speedy growth of bone about the socket of the tooth.

To this end, a prosthetic tooth or denture of the invention is provided with a means for generating electrical current and transmitting the same to the socket of the denture to induce the growth of callus about the socket.

The prosthetic denture or device of the invention, according to one embodiment, may be provided with an implant or base portion which is implanted in bone adjacent an oral cavity and which serves as an electrode. An extremity of the implant or base portion is adapted to receive thereon a cap or crown which, for example, contains therein a small power source by which electrical current is supplied to the aforesaid electrode of the tooth and thereby promotes the growth of bone and at the same time induces bacterial stasis. In certain cases, chip microcircuitry may be installed in the prosthesis. Other means for supplying current to the socket may alternatively be employed such as by utilizing a bridge used for support and spanning across two adjacent teeth lying on either side of the prosthetic denture, the bridge containing therein a source of power.

In accordance with still another embodiment, the prosthetic denture may have a thermocouple which generates current. In still another embodiment, the prosthetic denture may be supplied with current via an external source of power connected to suitable transmission means inside the tooth. In yet another embodiment, the current may be produced by an immersion of two metals in the body fluid. Whichever form of the invention is employed, the electrical current passing through the socket portion which forms the embedded part of the tooth cuds in the growth of callus and prevents infection by anaerobic bacteria which quite often leads to trigeminal neuralgia. The comparative surface charges of the bone and the implant also, it is believed, aids in avoiding rejection of the prosthesis.

BRIEF DESCRIPTION OF THE DRAWINGS

The invetion will be more readily understood with reference to the following detailed description when taken in conjunction with the accompanying drawing, wherein.

DETAILED DESCRIPTION

Figure 1:
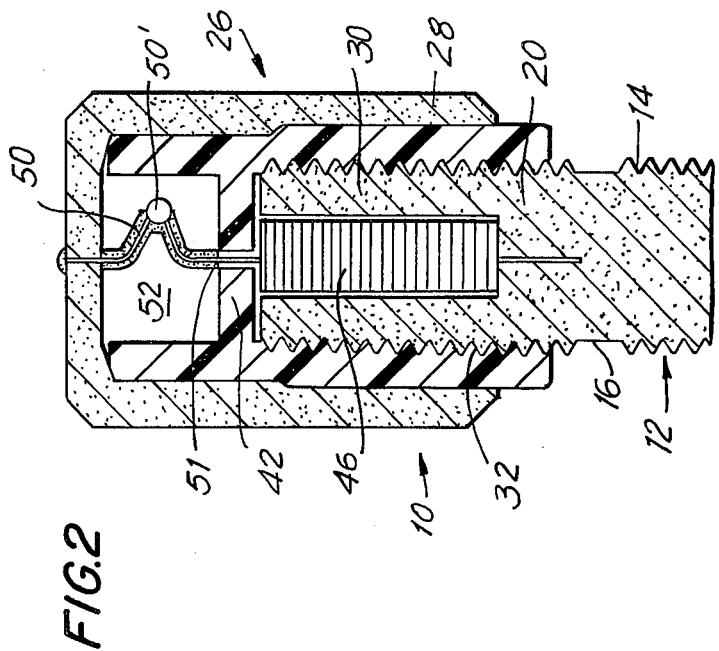
FIG. 1 is a cross-sectional diagrammatic view of an endosteal bionic tooth in accordance with a first embodiment of the invention.

In FIG. 1 is shown an endosteal bionic tooth 10 of the invention. The bionic tooth 10 socket or implant has a lower base socket or implant portion 12 of cylindrical shape which is adapted for being embedded in the bone of a jaw and which has on its circumference a first series of spiral grooves or thread 14 which aids in the locking of the lower socket portion 12 in the bone in which implantation is taking place.

A locking notch 16 is provided directly above the uppermost groove of thread 14, which further aids in locking the socket portion 12 in place in the bone. The socket portion 12 has an upper extension 20 which is formed with a second series of circumferential spiral grooves on thread 22 for mating engagement with spiral ridges on thread 24 in the upper or crown portion 26 of the bionic tooth 10.

The upper portion 26 of bionic tooth 12 houses therein a means for supplying electrical current to the socket portion 12 of the tooth. The upper portion 26 includes an outer sleeve-like portion 28 which constitutes the oral electrode of the tooth. The portion 28 houses therein an insulating member 30 which insulates the electrode 28 from the socket portion 12 which constitutes the other or bone-embedded electrode.

The portions 12 and 28 constituting the electrodes are made of any suitable material which will conduct electricity such as, for example, high density carbon or vitreous carbon. The insulating member 30 may be of any suitable material that prevents the direct conducting of the current between portions 12 and 28.

The insulating member 30 has an H shaped cross-section and comprises in its lower portion 30' inner circumferential spiral ridges or thread 24 which mates with the spiral grooves 22 of the socket portion 12 so as to hold the parts together in threaded manner.

The upper portion 30" of the insulating member 30 houses therein a battery 36 which, via a lead 38 passing through an aperture 40 in the cross bar portion 42 of the insulating member, is electrically connected to a resistor 46 housed within the upper portion of the socket portion 12. The resistor 46 has a lead 48 which is electrically connected to the bone-embedded electrode or socket portion 12. Although not shown in the drawing, the socket portion 12 is electrically connected in closed circuit with the oral electrode or sleeve-like portion 28 through the bone and gum tissue.

In the specific form of the embodiment shown in FIG. 1, the oral electrode or sleeve-like portion 28 constitutes the cathode and is connected to the positive terminal of the battery 36, while the bone-embedded electrode or socket portion 12 constitutes the anode and is connected to the negative terminal of the battery 36. It is to be understood that under certain circumstances the oral electrode or sleeve-like portion 28 may be the anode while the bone embedded electrode or socket portion 14 may be the cathode.

When the bionic tooth 10 of the invention has been implanted, the battery 36 will supply current to the socket portion 12 which is embedded in the bone and will aid in the formation of the bone and at the same time prevent infection. Withdrawal of the bone from the implant will be avoided. The formation of callus may take place along the line of force induced by the current, as has been disclosed in the article "Mechanical and Electrical Callus" by Iwao Yasuda referred to above.

When the bionic tooth is adequately supported by the bone, the upper portion 26 of the tooth may be removed by unscrewing the insulating member 30 and substituting a suitably shaped permanent crown member having spiral ridges or thread to mate with the thread 22. The battery 36 and the resistor 46 may be of such design as to supply current to the socket portion in a range, for example, of from 1-pico-ampere to 100 micro-amperes. It has been found that a current of between 1 pico-ampere and 1 microamperes performs best in producing osseous and cartilagenous growth without any accompaniment of necrosis.

Since it has been found that the type of bone tissue growth, that is bony, cartilagenous, fibrous, or necrotic, is directly dependent upon the amount of energy supplied, it is possible to replace the direct source of current 36 with an alternating one.

Figure 2:
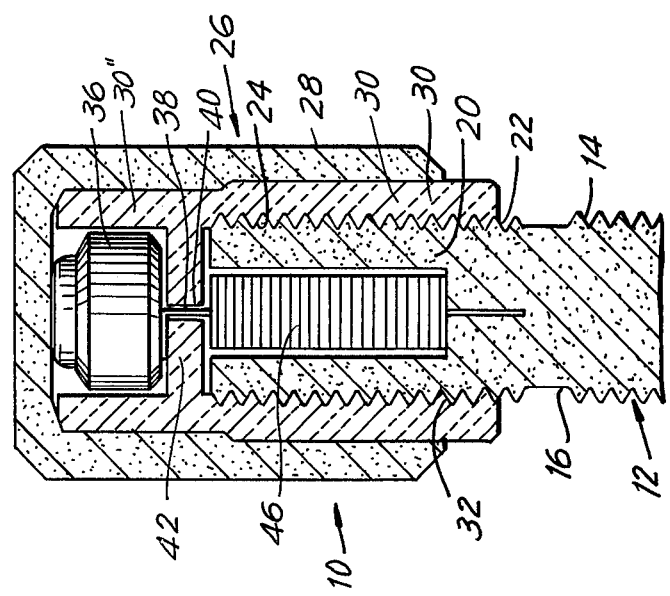
FIG. 2 is a cross-sectional view of an endosteal bionic tooth in accordance with a second embodiment of the invention.

In FIG. 2, there is shown a modification of the bionic tooth in accordance with a second embodiment of the invention. Instead of the battery used in FIG. 1, a thermocouple 50 having a junction 50' is used having one terminal end 51 in electrical communication with the resistor 46 and the other end in electrical connection with the oral electrode 28.

A chamber 52 housing the thermocouple 52 is filled with a thermally conductive epoxy filling or air. It will be appreciated that due to the temperature in the oral cavity, there will be caused a flow of current to the socket portion 12. The embodiment of FIG. 2 is used in the same manner as described for the embodiment of FIG. 1.

In the aforegoing discussion of bionic teeth of the invention, it has been indicated that the socket portion 12 has spiral grooves 14 formed therein for aiding in the implantation thereof. However, it is possible to include instead of this threaded pin arrangement, which is well-known in the art, numerous other forms of socket portions or substitutions therefor. For example, it is possible to use such well-known socket arrangements as Frank's conical pin, Scialom's tripod, Cherchev's ridge spiral, or Linkow's blade.

Instead of using a power source contained within the bionic tooth itself, it is possible to provide a source of power to the socket portion via an external source. For example, the bridge used in implanting the bionic tooth may itself comprise a source of power for supplying current to the socket portion. Alternatively, the bridge itself can be connected to a source of power provided externally of the bridge. In still another form, the source of power may be supplied to the socket portion by using the socket portion as one electrode and implanting another electrode in the bucklum ucova, both of which electrodes are connected to a battery or other source of power implanted subcutaneously.

In another form of the invention, two metals can be arranged in series in the prosthesis to be immersed in the body fluids for the generation of current.

While specific embodiments of the invention have been shown and described, it is to be understood that numerous changes and modifications may be made without departing from the scope and spirit of the invention.

Figure 3:
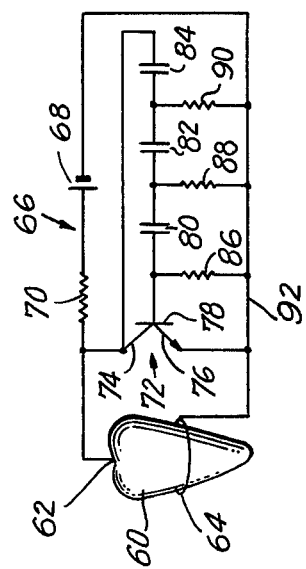
FIG. 3 is a diagrammatical view illustrating chip microcircuitry which in the actual construction is incorporated into the prosthesis structure.

FIG. 3 illustrates another form of the invention according to which the electrical energy is provided in the form of A.C. current. In FIG. 3 is diagrammatically illustrated the prosthesis 60, one electrode of which appears at 62. The other electrode is diagrammatically indicated at 64 as encircling the prosthesis. A chip microcircuit 66 is schematically indicated. This circuit is, according to know technology, of extremely small size and is adapted for being accommodated within a cavity provided within the crown of the tooth. The microcircuit is intended to cooperate with a battery such as indicated at 68 which is incorporated into the structure in a manner generally set forth hereinabove.

The microcircuit includes a resistor 70 coupled to electrode 62 and a transistor 72 having a collector 74 and emitter 76 and a base 78. The base is connected in a loop with the collector 74 through a series of capacitors 80, 82 and 84. Resistors 86, 88 and 90 are connected from terminals of the aforesaid capacitors to a line 92 which is coupled to the electrode 64 as well as via battery 68 to resistor 70. The circuit functions to convert the D.C. current of the battery to A.C. current in known manner and can be designed to provide preferably a frequency of 0.5 to 1 mHz.

In the embodiments of the invention, it is preferred that the electrical energy be supplied at a constant voltage.

What is claimed is:

1. An endosteal bionic tooth comprising:
an implant socket portion for implantation into bone, a crown portion attached to said lower socket portion and extending therefrom and means for supplying energy to said implant socket portion for inducing the formation of callus and for preventing infection.

2. An endosteal bionic tooth according to claim 1, wherein said implant socket portion comprises means for locking said bionic tooth in the bone around said implant socket.

3. An endosteal bionic tooth according to claim 2, wherein said implant socket portion is of an electrically conductive material, and said means for supplying energy to said implant socket portion comprises a source of electrical current, which supplies current at a constant voltage to said implant socket portion to promote the growth of callus and to prevent infection.

4. An endosteal bionic tooth according to claim 3, wherein said implant socket portion and said crown portion comprise attaching means for attaching said portions together, said crown portion further comprising a sleeve-like outer member made of an electrically conductive material, said sleeve-like outer member constituting an electrode for said means for supplying energy to said implant socket portion, and an insulating member insulating said outer member from said implant socket portion.

5. An endosteal bionic tooth according to claim 4, wherein said attaching means comprises a series of spiral ridges on the inner circumference of said insulating member and a series of spiral grooves on the outer circumference of said insulating member for mating engagement with said spiral ridges on said insulating member.

6. An endosteal bionic tooth according to claim 3, wherein said means for supplying energy to said implant socket portion further comprises a resistor in said implant socket portion electrically connected to said source of electrical current, said resistor having a first end electrically connected to said source of electrical current and a second end electrically connected to said implant socket portion, said implant socket portion constituting one electrode for said means for supplying energy to said implant socket portion.

7. An endosteal bionic tooth according to claim 6, wherein said source of electrical current comprises a battery, said crown portion housing said battery therein, said battery having a first terminal electrical communication with said crown portion and a second terminal in electrical communication with said implant socket portion.

8. An endosteal bionic tooth according to claim 3, wherein said source of electrical current comprises a thermocouple having a first terminal end electrically connected to said crown portion and a second terminal end electrically connected to said implant socket portion whereby body temperature causes a flow of current to said implant socket portion.

9. An endosteal bionic tooth according to claim 8, wherein said thermocouple is housed in said crown portion, said crown portion being provided with a cavity therein and a thermally conductive medium in the cavity in which said thermocouple is housed.

10. An endosteal bionic tooth according to claim 9, wherein said implant socket portion and said crown portion comprise attaching means for attaching said implant socket portion and said crown portion together, and said crown portion further comprises a sleeve-like outer member made of an electrically conductive material, said sleeve-like outer member constituting an electrode for said thermocouple, and an insulating member insulating said outer member from said implant socket portion.

11. An enodsteal bionic tooth according to claim 10, wherein said attaching means comprises a series of spiral ridges on the inner circumference of said insulating member and a series of spiral grooves formed on the outer circumference of said implant socket portion for the mating engagement with said spiral ridges on said insulating member.

12. An endosteal bionic tooth according to claim 3, wherein said upper portion and said lower socket portion are made of electrically conductive vitreous carbon.

13. An endosteal bionic tooth according to claim 3, wherein said means for supplying energy comprises microcircuitry in at least one of such portions, said microcircuitry being in electrical communication with said source of electrical current for producing A.C. current.

14. A method of implanting an endosteal bionic tooth in which the growth of callus is promoted and infection prevented, said method comprising: implanting at least a portion of the endosteal bionic tooth in bone adjacent an oral cavity in which the tooth is to become permanent; and supplying energy to the tooth portion.

15. A method according to claim 14, wherein the step of supplying energy to said tooth portion comprises supplying electrical current in an amount of 1 pico-ampere and 100 microamperes and at a constant voltage.

16. A method according to claim 14, wherein said step of supplying electrical current comprises implanting an electrode in the bucklum ucova of said oral cavity, electrically connecting said electrode with said portion, and electrically connecting said electrode with a source of current.

17. A method according to claim 15, wherein said step of supplying electrical/current comprises physically and electrically connecting a crown portion to the first said tooth portion and to a source of current, and locating a source of said current in the crown portion.

18. A method according to claim 17, further comprising removing the crown portion from the first said portion when the growth of callus about the first said portion is adequate, and attaching to the first said portion a permanent crown which together with the first said portion forms an endosteal basic tooth.

* * * * *